United States Patent
Kleyman et al.

(10) Patent No.: US 7,901,384 B2
(45) Date of Patent: Mar. 8, 2011

(54) DOSAGE DEVICE

(75) Inventors: Gennady Kleyman, Brooklyn, NY (US); Alexander Merson, Brooklyn, NY (US)

(73) Assignee: Algen & Klemer LLC, Brooklyn, NY (US)

( * ) Notice: Subject to any disclaimer, the term of this patent is extended or adjusted under 35 U.S.C. 154(b) by 1476 days.

(21) Appl. No.: 11/316,217

(22) Filed: Dec. 21, 2005

(65) Prior Publication Data

US 2006/0184136 A1     Aug. 17, 2006

Related U.S. Application Data

(63) Continuation-in-part of application No. 10/900,731, filed on Jul. 28, 2004, now abandoned.

(51) Int. Cl.
*A61M 5/00* (2006.01)
(52) U.S. Cl. ............... 604/207; 604/208; 604/210
(58) Field of Classification Search .......... 604/207–208, 604/210, 110, 220
See application file for complete search history.

(56) References Cited

U.S. PATENT DOCUMENTS

| | | | | |
|---|---|---|---|---|
| 5,328,476 | A | * | 7/1994 | Bidwell ............ 604/110 |
| 2004/0158205 | A1 | | 8/2004 | Savage |
| 2005/0277882 | A1 | | 12/2005 | Kriesel |

OTHER PUBLICATIONS

International Preliminary Report on Patentability for International Application No. PCT/US05/026705, Dated Jan. 30, 2007.

* cited by examiner

*Primary Examiner* — Kevin C Sirmons
*Assistant Examiner* — Deanna K Hall
(74) *Attorney, Agent, or Firm* — Leason Ellis LLP

(57) ABSTRACT

A dosage device has a hollow barrel and a plunger slidable within the barrel, and a plurality of formations provided on the barrel and plunger and cooperating with one another to produce a sound signal and a pointed impulse, which corresponds to a predetermined dosage of fluid drawn into or displaced from the barrel. At least one of the barrel and plunger formations which are made of flexible material is configured to have a plurality of spaced-apart segments shaped and dimensioned to improve the quality of the sound signal.

11 Claims, 8 Drawing Sheets

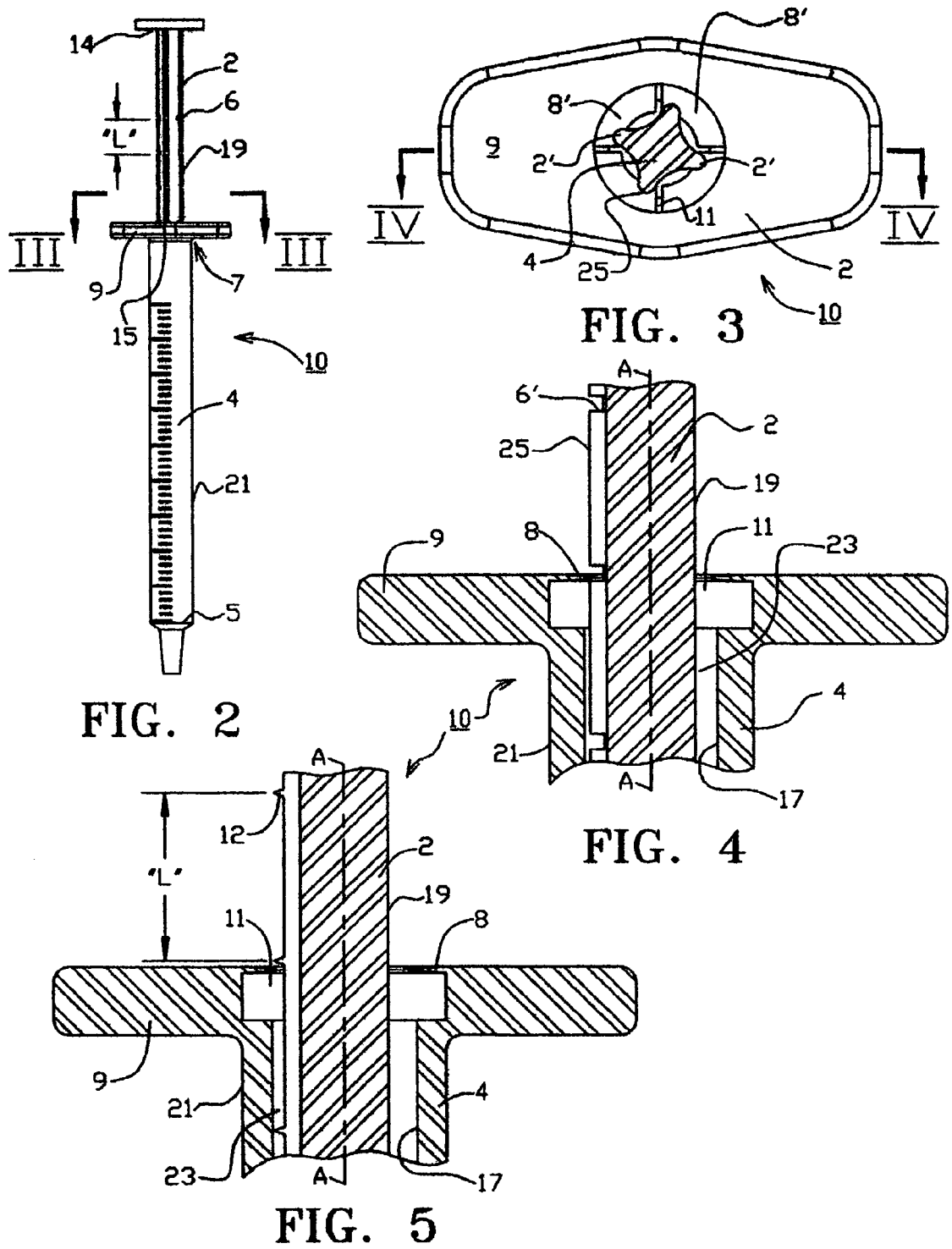

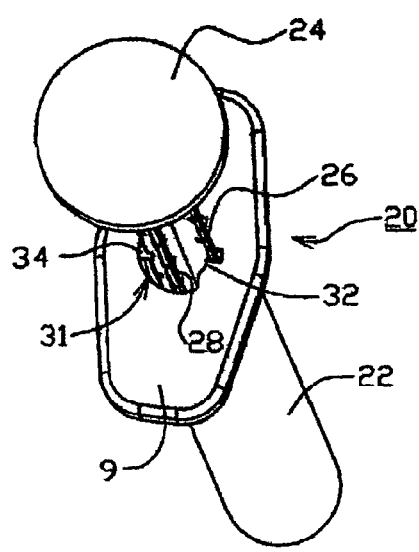
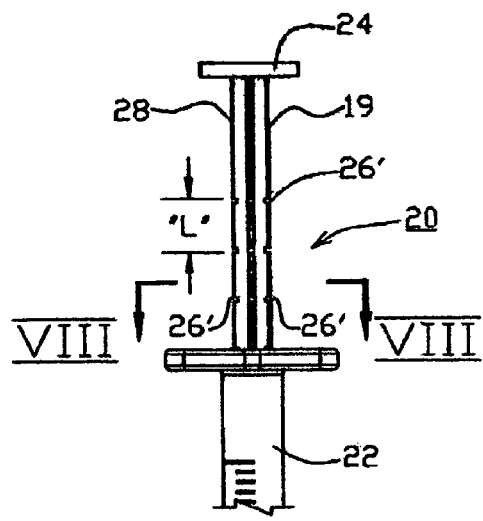
FIG. 6
FIG. 7
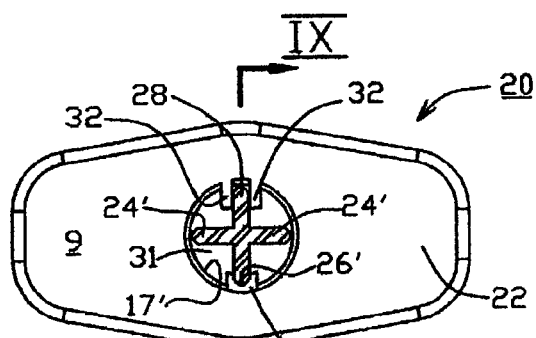
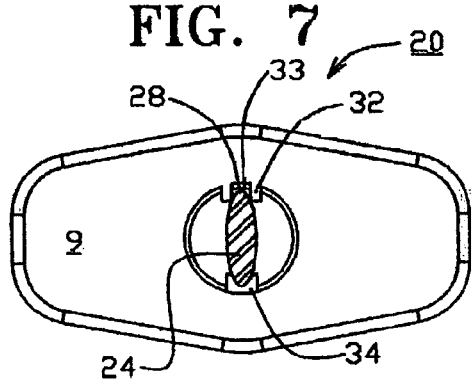
FIG. 8
FIG. 8A
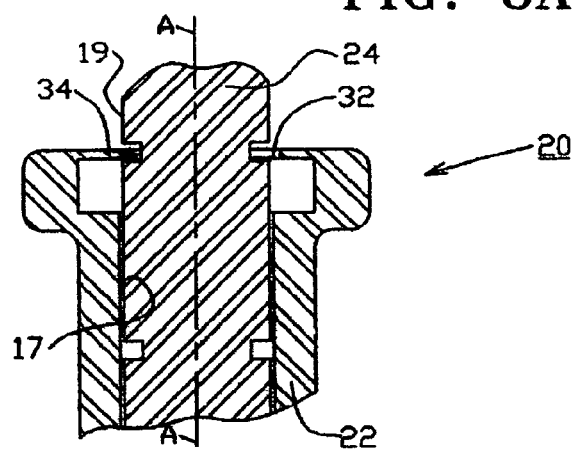
FIG. 9

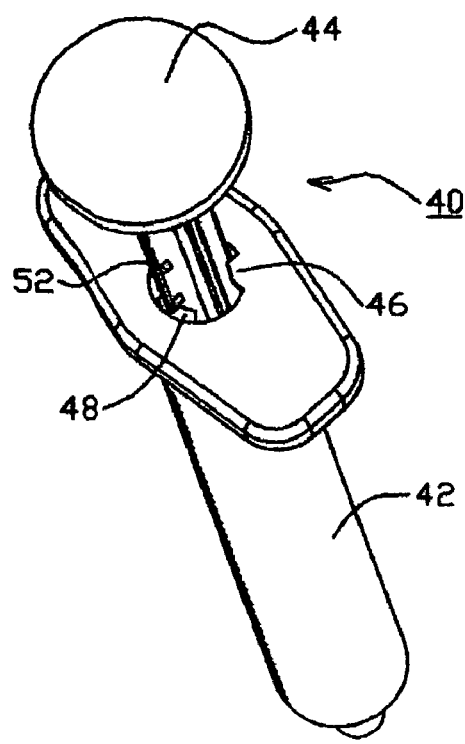
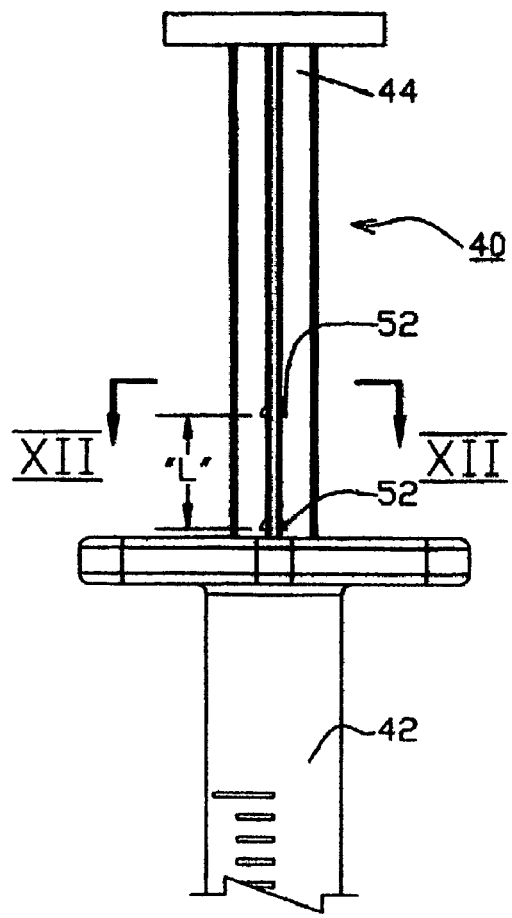
FIG. 10  FIG. 11
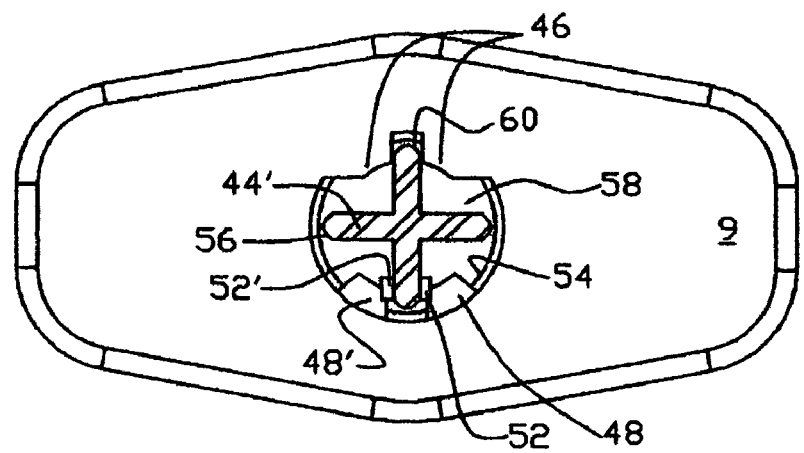
FIG. 12

DOSAGE DEVICE

CROSS REFERENCE TO RELATED APPLICATION

The present application is a continuation-in-part of U.S. application Ser. No. 10/900,731 filed Jul. 28, 2004, now abandoned, which is hereby incorporated by reference in its entirety.

TECHNICAL FIELD

This invention relates to fluid dispensing devices, and more particularly, the invention relates to dosage devices for storing, drawing, and administering a predetermined dosage of fluid.

DESCRIPTION OF THE RELATED ART

Devices for drawing and administering predetermined amounts or dosages of fluid are widely used in a variety of industries including, but not limited to, medicine. Dosage devices, such as hypodermic syringes, administer the drug directly in the bloodstream or in the tissue of the patient, who is thus directly affected by the drug. As a result, it is very important to assure that the precise dosage is administered at all times.

Commonly, hypodermic syringes include a graduated scale disposed on the body of the syringe. Utilizing the scale, an individual administering a drug will draw a quantity of the drug from a vial into the syringe, and then expel quantities of the drug until the precise dosage is achieved. This common measurement procedure can often be difficult and time-consuming, and more importantly, can be quite wasteful, as a quantity of the drug is often discarded in order to achieve the appropriate dosage.

Quite often, medical professionals administering an injection may not have a clear view of the targeted body part of the patient. In this case, many rely on their experience to administer the desired dosage, which still may not be precise. Furthermore, those individuals who self-administer drugs may experience even more inconvenience than the professionals. Diminished hearing, eyesight and/or diminished dexterity of the user may lead individuals to draw or dispense an imprecise dosage of the drug into, or from the syringe. More significantly, it may lead them to draw or dispense an insufficient or excessive dosage into their body, which can result in life-threatening or worse, fatal, consequences.

To minimize the aforementioned inconveniences, some of the known dosage devices have been provided with a tactile mechanism operative to generate a sound signal and/or increased resistance indicating displacement of the desired dosage of fluid into and from the dosage device.

A need thus exists for dosage devices that have a structure configured to reliably produce a distinct audible and tactile signal to the user indicating that the desired dosage of fluid has been drawn into, or displaced from, the dosage devices in a reliable, simple fashion.

SUMMARY

The present invention is directed to dosage devices that satisfy these needs. The invention includes a dosage device capable of producing a clear indicating signal, such as sound and/or pointed impulse sensed by the user while either forcing fluid into or displacing it from its barrel.

The dosage device in accordance with the invention includes a barrel formation provided on a barrel and a plunger formation located on a plunger. The barrel and plunger formations are configured to engage one another during linear displacement of the plunger relative to the barrel and produce clear sound signals. One of the barrel and plunger formations is divided into a plurality of separate, spaced-apart segments. As a consequence, even if the plunger deviates from its predetermined path, a relatively short segment of one of the formations still produces a clear sound signal and a pointed impulse sensed by the user upon engaging the other formation as the plunger and barrel are linearly displaced relative to one another.

According to another embodiment, a dosage device includes a barrel extending along a longitudinal axis and including an interior space and a flange member formed at a proximal end of the barrel. The flange member includes a plurality of inwardly extending flexible tabs formed at a proximalmost location of the flange member, with each tab extending inwardly into an opening that is formed through the flange member and is axially aligned with the interior space of the barrel. The device also includes a plunger received in and axially displaceable within the interior space; and at least one plunger formation provided on an outer surface of the plunger. At least one of the plunger formations is configured to selectively engage at least one of the barrel flanges while generating an indicating signal corresponding to a predetermined dosage of fluid drawn into or dispensed from the barrel during axial displacement of the plunger.

According to another embodiment, a dosage device includes a barrel extending along a longitudinal axis and including an interior space and a flange member formed at a proximal end of the barrel. The flange member includes a plurality of plunger engaging members formed along an upper surface thereof. Each engaging member includes a catch formed at its most radially inward location, with the catch at least partially extending inwardly into an opening that is formed through the flange member and is axially aligned with the interior space of the barrel. The device also includes a plunger received in and axially displaceable within the interior space, and at least one plunger formation provided on an outer surface of the plunger. At least one of the plunger formations is configured to selectively engage at least one of the catches while generating an indicating signal corresponding to a predetermined dosage of fluid drawn into or dispensed from the barrel during axial displacement of the plunger.

In yet another embodiment, a dosage device assembly includes a barrel extending along a longitudinal axis and including an interior space and a flange member formed at a proximal end thereof. The assembly includes a dosing member that is configured to be removably attached to the flange member. The dosing member has a body that includes a plurality of resilient segments formed circumferentially about an opening formed through the body of the dosing member and defined by a plurality of slits formed in the body. Inner edges of the segments define the opening and at least partially extend over the interior space, with the opening of the dosing member being axially aligned with the interior space of the barrel.

These and other features and aspects of the present invention will be better understood with reference to the following description, figures, and appended claims.

BRIEF DESCRIPTION OF THE DRAWING FIGURES

The above and other aspects and advantages of the present invention will be more clearly understood from the following detailed description taken in conjunction with the accompanying drawings, in which:

FIG. 2 is a side elevation view of the dosage device shown in FIG. 1;

FIG. 3 is a cross-sectional view of the plunger of the dosage device taken along the line III-III of FIG. 2;

FIG. 4 is a cross-sectional sectional view of the dosage device taken along the line IV-IV of FIG. 3, illustrating a projection that is formed on the barrel's inner surface, and an indentation that is provided on the plunger's outer surface;

FIG. 5 is a cross-sectional view of the dosage device similar to FIG. 4, but illustrating the projection, which is provided on the outer surface of the plunger and the indentation on the inner surface of the barrel;

FIG. 6 is a top perspective view of the dosage device configured in accordance with a second embodiment of the present invention;

FIG. 7 is a side elevation view of the dosage device shown in FIG. 6;

FIG. 8 is a cross-sectional view of the plunger of the dosage device taken along the line VIII-VIII of FIG. 7;

FIG. 8A is a cross-sectional view of the plunger having a cross-section different from the one illustrated in FIG. 8;

FIG. 9 is a sectional view of the dosage device taken along the line IX-IX of FIG. 8 and illustrating a projection, which is provided on the outer surface of the plunger, and an indentation, which is formed on the inner surface of the barrel;

FIG. 10 is a perspective view of the dosage device configured in accordance with a third embodiment of the invention;

FIG. 11 is a side elevation view of the dosage device shown in FIG. 10;

FIG. 12 is a cross-sectional view of the plunger of the dosage device taken along lines XII-XII of FIG. 11;

DETAILED DESCRIPTION OF PREFERRED EMBODIMENTS

Figure 1:
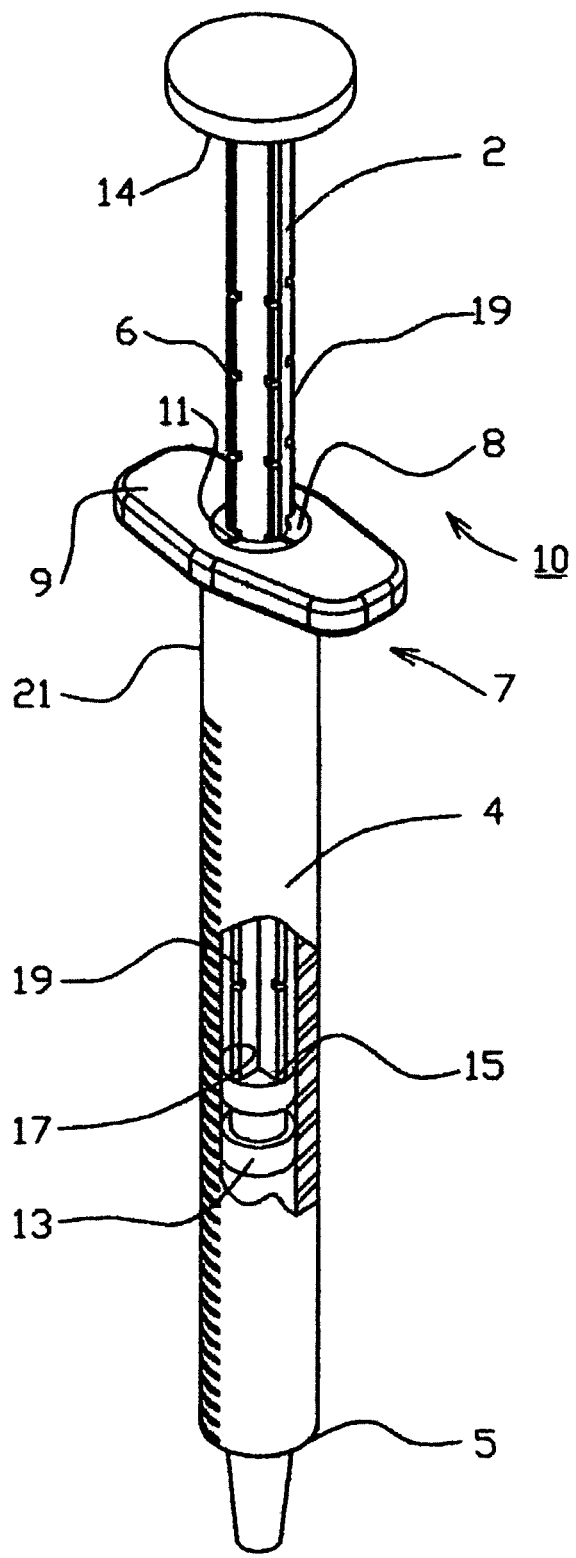
FIG. 1 is a perspective view of a dosage device configured with a plunger and barrel according to a first embodiment of the present invention.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, left, right, up, down, over, above, below, beneath, rear, and front may be used with respect to the drawings. These and similar directional terms should not be construed to limit the scope of the invention in any manner. The terms "dosage device" and "hypodermic syringe" are used interchangeably.

Referring more particularly to the drawings, FIGS. 1-5 illustrate a dosage device 10 including, but not limited to, a hypodermic syringe, which is operative to receive, store and dispense predetermined dosages of fluid. A clear sound signal accompanies each predetermined dosage drawn into the syringe or dispensed therefrom. Furthermore, the user experiences increased resistance during displacement of the components of the dosage device indicated by a pointed impulse every time the predetermined dosage of fluid has been displaced.

The hypodermic syringe 10 includes a hollow barrel 4, which serves as a reservoir for fluid and slidably receives the plunger 2 acting as a means for displacing fluid into and out of the barrel 4. A distal end 5 of the barrel 4 (FIGS. 1 and 2) is coupled to a hypodermic needle traversed by fluid on its way in and out from the barrel 4. Linear displacement of the plunger 2 from the distal end 5 of the barrel towards the barrel's proximate end 7 forces fluid into the barrel; the opposite direction of the plunger's displacement is associated with evacuation of the accumulated fluid from the barrel. To complete evacuation of fluid from the barrel 4, the plunger 2 is displaced so that the plunger's distal end 15 is located next to the distal end 5 of the barrel. Conversely, to fully fill the barrel 4, the plunger is displaced so that its distal end 15 is juxtaposed with the proximal end 7 of the barrel, as illustrated in FIG. 2.

The proximal end 7 of the barrel 4 has a flange 9 configured to provide a support for the user's fingers, while the user actuates the plunger 2 to move linearly relative to the barrel 4. The flange 9 extends radially beyond an outer surface 21 of the barrel 4 (FIGS. 1 and 4-5) and thus has a sufficiently large support area for the user's convenience. The flange 9 has an opening 11 (FIGS. 1 and 2) coaxial with a passage 23 (FIGS. 4 and 5), which is defined by the inner surface 17 of the barrel 4, and traversed by the plunger 2. Dispensing of fluid associated with linear motion of the plunger 2 towards the distant end of the barrel 4 is terminated when the proximal end 14 of the plunger reaches the top of the flange 9.

The opening 11 of the flange 9 is dimensioned to be slightly larger than an outer surface 19 of the plunger 2 (FIGS. 1 and 3-5). However, to guide the plunger 2 along the desired linear path through the flange 9, the opening 11 is partially obstructed by a barrel formation 8 (FIGS. 1, 3-5) extending radially inwards from the opening's periphery. The barrel formation(s) 8 is made from flexible material, such as engineering plastics or rubber, and dimensioned to extend so that it terminates next to the outer surface 19 of the plunger. The plunger 2, in turn, has a plurality of plunger formations 6 (FIGS. 1-4) spaced from one another along an axis A-A (FIG. 4) at a predetermined distance L (FIG. 2). As the plunger 2 moves relative to the barrel formation 8, each of the plunger formations 6 engages the barrel formation 8 to produce a sound signal. Consecutive sound signals and/or pointed impulses produced by the formations during displacement of the plunger 2 at the distance L indicate that a predetermined dosage of fluid has entered or exited the barrel 4. Attempts to continue displacement of the plunger 2 after the formations 6, 8 have been engaged are associated with a substantial effort necessary to overcome the resistance of the engaged formations. While the plurality of plunger formations 6 is shown in FIGS. 1-2 and 4, a single plunger formation may be sufficient, if the device 10 is specifically designed to operate as a single dosage device.

To produce a distinct sound signal the barrel formation 8 is provided with multiple segments 8' (FIG. 3), which are spaced angularly around the periphery of the opening 11. Thus, having multiple segments instead of a single endless formation allows a relatively small segment 8' to be substantially more flexible than the endless formation and produce a clear sound signal upon engagement with the plunger formation 6. Each segment 8' may be curved, as shown in FIG. 3, polygonal or have any other irregular shape subject only to reliable engagement with the formation 6. Furthermore, the segments 8' may be non-uniformly shaped and spaced angularly from one another at a non-uniform distance.

Each of the plunger formations 6 may be segmented as well. Since, as shown in FIGS. 1-4, the barrel formation 8 is configured as a projection, each plunger formation 6 includes an indent receiving the projection. The quality of sound or pointed impulses would not be affected if the plunger formation 6 were formed as an endless indentation or as a plurality of spaced angularly apart indentations, as shown in FIGS. 1 and 2.

Referring to FIG. 5, the plunger 2 has a plurality of the plunger formation 12 spaced from one another along the axis A-A and each configured as a respective projection with multiple segment, which are angularly spaced from one another. The formations 12 are made from flexible material producing sound signals and/or pointed impulses to the user's finger due the change of resistance caused by engagement between each plunger formations 12 and barrel formation 8. In this case, the barrel formation may be made from either rigid or flexible material. The flange 9, in turn, includes the barrel formation 8 configured as an endless or segmented indentation. Regardless of the specific configuration of the formations, the width of the indentation, as viewed along the longitudinal axis A-A (FIGS. 4 and 5), is somewhat greater than the thickness of the projection 12 which improves the quality of sound signals.

Turning to FIGS. 3 and 4, the plunger 2 is configured with a cross-section having a cross-like shape. Each of multiple legs 2' of the plunger extends radially outwards towards the periphery of the opening 11 provided with multiple segments 8'. The legs 2' and segments 8' of the projection 8 are dimensioned to radially overlap, which allows the segments 8' to penetrate the indentations 6' (FIG. 4) once the formations 6 and 8 are radially aligned. Four indentations 6' forming the plunger formation 6 each are provided on a respective outer longitudinal edge 25 of the leg 2' (FIGS. 3 and 4). If a double or greater number of predetermined dosages of fluid is required, the user continues to move the plunger 2 to generate the desired number of consecutive sound signals. When not engaged within indentations 6', the segments 8' (FIG. 3) urge against the outer edges 25 of the legs 2', which define the outer surface 19 of the plunger 2. The cross-section of the plunger 2 is not limited to the one shown in FIG. 3, but can have any of circular, polygonal or irregular shapes.

Referring again to FIG. 1, the distal end 15 of the plunger has a seal 13 typically made from polymer, such as rubber or plastic, and extending between the outer surface 19 of the plunger 2 and an inner surface 17 of the barrel 4. Penetration of fluid through the seal 13 causes the syringe 10 to malfunction. Therefore, the seal 13, displaceable with the plunger 2, presses against the inner surface 17 of the barrel with a force sufficient to prevent fluid from penetration into a space between the seal 13 and the proximal end 7 of the barrel.

The components of the dosage device 10 are typically made from engineering plastics. However, various materials may be successfully utilized as well. For example, the plunger 2 and plunger 4 may be made from glass. Alternatively, material of one of these components may be glass, whereas the other component is made from plastic. Furthermore, material of the plunger and barrel may be different from material of the plunger and barrel formations. For example, while material of the plunger 2 may include glass, plunger's formations may be formed of plastic, and conversely. To implement such a modification technologically, the body of the barrel may be recessed at axially spaced-apart locations, and plastic segments may be removably or fixedly mounted to these recessed locations.

Referring to FIGS. 6-9, a dosage device 20 is configured in accordance with a further embodiment of the invention. Similarly to the device 10 illustrated in FIGS. 1-5, the dosage device 20 has a barrel 22, receiving a plunger 24, and barrel and plunger formations 34 and 26, respectively. Displacement of the plunger 24 at a distance L (FIG. 7) between axially adjacent plunger formations 26 corresponds to the predetermined fluid dosage entering or exiting the dosage device 20.

Displacement of fluid into or from the barrel 22 is associated with sound signals produced by the engaged formations 26 and 34 and increased resistance to displacement of the plunger 24 as a result of engagement between these formations. The barrel formation 34 including a projection, which extends from an inner surface 17' (FIG. 8) of opening 31 towards the outer surface 19 of the plunger 24 (FIGS. 7 and 8), is received by an opposing segment 26' of the plunger formation 26. Accordingly, each plunger formation 26 includes at least two indentations or segments 26' each provided on respective longitudinal edge 28 (FIG. 7) of a leg 24' of the cross-shaped plunger.

As shown in FIG. 8, a single barrel projections/formation 34 is sufficient to reliably engage and produce a sound signal. However, multiple projections may be spaced diametrically opposite one another or at any other angle differing from 180° and each received in a respective indentation 26'.

In contrast to the barrel formation 8 illustrated in FIGS. 1-5, the barrel formation 34 (FIGS. 6-9) is not symmetrically arranged relative to axis A-A (FIG. 9). The circumference of the inner surface 17' of the opening 31 (FIGS. 6 and 8) formed in the flange 9 has a circular portion and a pair of non-circular portions 32. The non-circular portions 32 are configured to form a recess 33 dimensioned to receive the edge 28 of the plunger's leg 24'. Engagement between the recess 33 and leg 24' prevents relative rotation between the plunger 24 and barrel 22 about the axis A-A (FIG. 9) preserves the integrity of the seal 13 (FIG. 1). Although the recess 33 has a generally U-shaped cross-section, this shape can vary as long as the shapes of the edge 28 of the plunger and recess 33 are complementary.

Note that the cross-section of the plunger 24 is not limited to the cross-like shape and can be circular, elliptical, as shown in FIG. 8A, polygonal or irregular. To prevent relative rotation between the plunger 24 and barrel 26, edges 28 (FIG. 8A) are dimensioned and shaped to engage the recess 33. Other configurations of the plunger 24 can be provided with a radial extension, such as a rib, to function similarly to the edges 28 (FIGS. 6 and 8A).

Moreover, instead of the recess 33 formed in the periphery of the opening 31 of the flange 9, a short, relatively thick guide extending radially towards the plunger 24 can be provided on the opening's inner surface 17. To limit relative rotation between the plunger and barrel 24, 22, the guide may be received in an axial groove formed along the plunger.

Referring to a further embodiment of a dosage device 40 configured in accordance with the invention and illustrated in FIGS. 10-12, the device 40 includes a plunger 44 slidable within a hollow barrel 42. Similarly to the previous embodiments, the plunger 44 has a plurality of plunger formations 52 spaced axially from one another at a distance L (FIG. 11), and the barrel 42 is provided with a barrel formation 48 (FIGS. 10 and 12). Displacement of the plunger 44 relative to the barrel 42 is accompanied by a sound signal when the barrel and plunger formations engage one another.

Turning to FIG. 12, both the barrel formation 48 and plunger formation 52 project from respective inner and outer surfaces 54, 56 of an opening 58 and plunger 44, respectively. Also, each of the barrel and plunger formations is segmented. Segments 48' of the barrel 42 are spaced angularly from one another at a distance sufficient for a leg 44' of the plunger 44 to slide between these projections. Increased resistance to displacement of the plunger 44 and generation of sound signals are caused by segments or lips 52' of the plunger formation 52, which flank the leg 44' and overlap the juxtaposed segments 48' of the barrel formation 52. Made from flexible material, all segments flex generating a sound signal upon engaging one another.

The surface 56 of the opening 58 of the flange 9 is shaped similarly to the opening 31 of FIGS. 6-9 and has a circular portion and two portions 46 defining a recess 60 which is dimensioned to receive a free end of the plunger's leg 44'. As a result, the plunger 44 and barrel 42 are rotationally fixed to prevent the seal 13 (FIG. 1) from damages.

In operation, the plunger is displaced towards and presses against the distal end of the barrel to assume an initial position. Displacement of the plunger towards the proximal end of the barrel is accompanied by a number of sound signals as each of the plunger formations passes the formation formed on the barrel's flange. As disclosed, each sound and/or change of resistance is indicative of a predetermined dosage of fluid filling the barrel. Reverse displacement of the plunger towards the distal end of the barrel is also accompanied by indicating signals informing the user how much liquid has been administered.

Referring more particularly to the drawings, FIGS. 13-16 illustrate a dosage device 100, according to one embodiment, including, but not limited to, a hypodermic syringe, which is operative to receive, store and dispense predetermined dosages of fluid. As described below, the device 100 is constructed to provide a clear auditory signal that accompanies each predetermined dosage drawn into the syringe or dispensed therefrom. Furthermore, the user experiences increased resistance during displacement of the components of the dosage device indicated by a pointed impulse every time the predetermined dosage of fluid has been displaced.

The dosage device 100 includes a hollow barrel 112 that serves as a reservoir for a fluid to be dispensed and slidably receives a plunger 120 that acts as a means for displacing the fluid into and out of the barrel 112. The barrel 112 includes a distal end 114 and an opposite proximal end 116, with the distal end 114 being coupled to a hypodermic needle (not shown) or some other source or receptacle of fluid. The hypodermic needle is coupled to the barrel 112 such that fluid can be either drawn from or introduced into the inside of the barrel 112. In particular, linear displacement of the plunger 120 from the distal end 114 of the barrel 112 towards the proximate end 116 of the barrel 112 forces fluid into the barrel 112; the opposite direction of displacement of the plunger 120 is associated with evacuation of the accumulated fluid from the barrel 112. To complete evacuation of fluid from the barrel 112, the plunger 120 is displaced so that a distal end of the plunger 120 is located next to the distal end 114 of the barrel 112. Conversely, to fully fill the barrel 112, the plunger 120 is displaced so that its distal end is juxtaposed with the proximal end 116 of the barrel 112.

The proximal end 116 of the barrel 112 has a flange member 130 configured to provide a support for the user's fingers, while the user actuates the plunger 120 to move linearly relative to the barrel 112. The flange 130 extends radially outward beyond an outer surface 117 of the barrel 112 and thus has a sufficiently large support area for the user's convenience. The flange 130 is thus formed around the body of the barrel 112 so it is it preferably coaxial with a passage or interior space 113 defined by the body of the barrel 112. The plunger 20 travels longitudinally within the interior passage or space 113. Dispensing of the fluid associated with linear motion of the plunger 120 towards the proximal end 116 of the barrel 112 is terminated when a proximal end 124 of the plunger 120 reaches the top of the flange 130.

Figure 13:
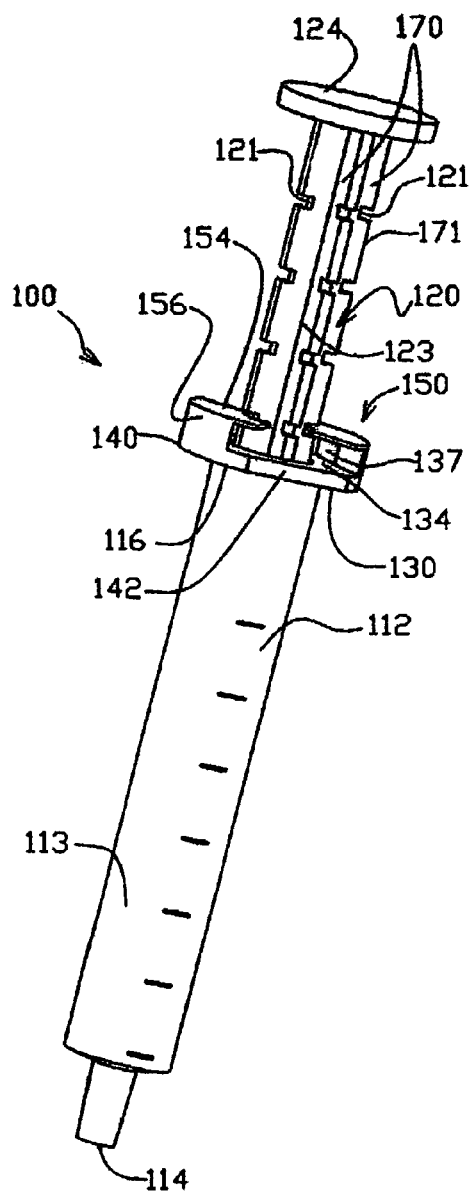
FIG. 13 is perspective view of a dosage device according to a fourth embodiment of the present invention.

In one embodiment described hereinafter with reference to FIGS. 21-24, the flange 130 is a separate component relative to the barrel 112. In each embodiment, the flange member 130 includes a flange body 132 that has an upper surface 134 and an opposing lower surface 136 that faces the distal end 114 of the barrel 112. The flange body 132 has a central opening 138 formed therein which is dimensioned so that at least a portion (e.g., distal end 114 of the barrel 112) can be received within the central opening 138 (i.e., the central opening 138 is axially aligned with the interior space 113). The dimension of the central opening 138 is sized relative to the diameter (outer diameter or greatest dimension) of the plunger 120 so as to permit the plunger 120 to freely move within the central opening 138 and be linearly displaced therein, but still sealingly contain the fluid in the barrel. The remaining portion of the flange body 132 extends radially outward therefrom. As shown in FIG. 13, the illustrated body 132 has a pair of arcuate ends 140 with a pair of side portions 142 being formed therebetween. In the illustrated embodiment, the side portions 142 are formed as flats and therefore, the two side portions 142 are in planes parallel to one another.

Figure 16:
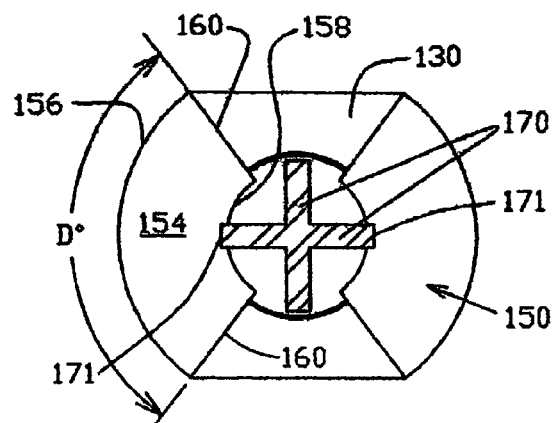
FIG. 16 is a cross-sectional view of the dosage device taken along line IV-IV of FIG. 14.
Figure 17:
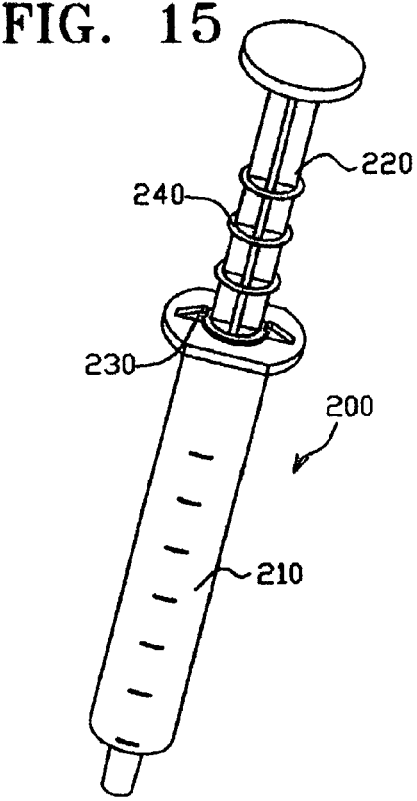
FIG. 17 is a perspective view of a dosage device according to a fifth embodiment of the present invention.
Figure 18:
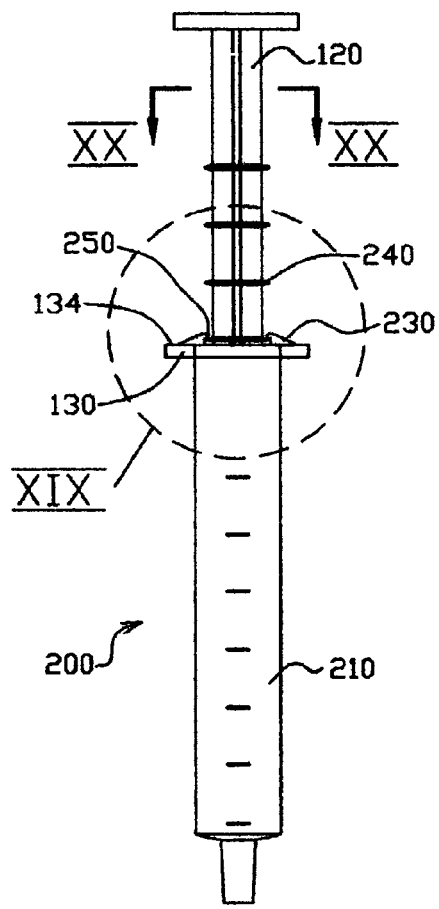
FIG. 18 is a side elevation view of the dosage device of FIG. 17.

In accordance with the present invention, to guide the plunger 120 along the desired linear path through the flange 130, the opening 138 is partially obstructed by a structure (formation) or an interference member, such as a flange or tab 150 that is designed to selectively contact and engage the plunger 120 as it moves axially and longitudinally within the central opening 138. More specifically, there is a pair of flanges or tabs 150 that each includes an upstanding wall 152 that extends upwardly from the upper surface 134 of the flange body 132 at one of the arcuate ends 40 and therefore, the upstanding wall 152 has a generally arcuate shape. At an upper edge of the upstanding wall 152, the flange 150 has an inwardly directed upper wall 154 that extends radially inward toward the central opening 138. As best shown in FIG. 16, the upper wall 54 is defined by an arcuate outer wall 156 that is above the arcuate end 140, an arcuate inner wall 158 that is spaced inwardly from the outer wall 156 and is generally above or at the edge of the central opening 138 and a pair of side edges 160 that extend between the outer wall 156 and the inner wall 158. The inner wall 158 is thus the portion of the tab that selectively engages the plunger 120.

Figure 14:
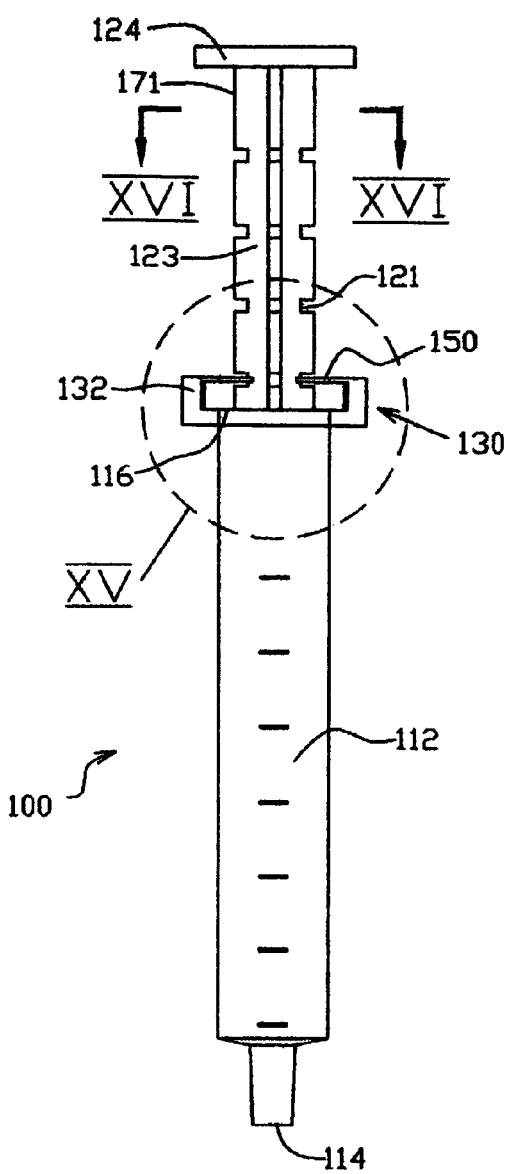
FIG. 14 is a side elevation view of the dosage device shown in FIG. 13.
Figure 15:
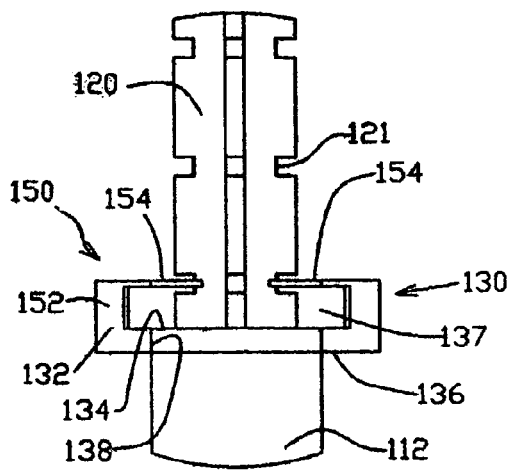
FIG. 15 is an enlarged sectional view taken alone the circle III of FIG. 14.

As shown in FIG. 16, an angle D is defined between the two side edges 160 of one upper wall 154. In one embodiment, the angle D is greater than 90 degrees and less than 180 degrees; and more particularly, in one embodiment the angle D is between 100 degrees and 150 degrees, e.g., between 120 degrees and 140 degrees. In one embodiment, one side edge 160 of one upper wall 154 lies within the same plane as a side edge 160 that is diagonally opposite and part of the other upper wall 154. The same arrangement is true of the other side edges 160. Since the upper walls 154 lie above the upper surface 134 of the flange body 132, a space or gap 137 is formed therebetween as illustrated in FIG. 14.

At least the upper walls 154 are preferably formed of a flexible material, such as engineering plastics or rubber, and dimensioned to extend inwardly toward the central opening 138 such that it selectively contacts and engages the plunger 120 so as to retain the plunger 120. In accordance with the present invention, the plunger 120 has features that are complementary to the tabs 150 to permit the two to selectively yet releasably interlock. According to one embodiment, shown in FIGS. 13-16, the plunger 120, in turn, has a plurality of plunger formations or complementary engaging features 121 spaced from one another along a longitudinal axis along a length of the device 100 and at a predetermined distance from one another. As the plunger 120 moves relative to the tabs 150, one or more of the plunger formations 121 engages one of the tabs or flanges 150 to produce a sound signal and/or pointed impulse or sound signals and/or pointed impulses of more than one formation engaging the tabs 150. Consecutive sound signals and/or pointed impulses produced by the formations during displacement of the plunger 120 at the distance between the plunger formations 121 indicate that a predetermined dosage of fluid has entered or exited the barrel 112. Attempts to continue displacement of the plunger 120 after the plunger formations 121 and the flexible tabs 150 have been engaged are associated with a substantial effort necessary to overcome the resistance of the engaged members 121, 150. While a plurality of plunger formations 121 is shown in FIGS. 13-16, a single plunger formation 121 may be sufficient, if the device 100 is specifically designed to operate as a single dosage device.

Although each of the illustrated indentations 121 has a generally U-shaped cross-section, this shape can vary as long as the shapes of the tab 150 and the indentation 121 are complementary.

In the illustrated embodiment, the plunger 120 has an elongated body 123 that extends its length and is formed as a plurality of rail-like sections (legs) 170 that are integrally attached to one another. In the illustrated embodiment, there are four rail sections 70 that are oriented 90 degrees apart such that the cross-section of the elongated body 123 has an X-shape. Each of the rail sections 170 has at least one and preferably a plurality of spaced plunger formations 121. More specifically, the plunger formations 121 are formed in spaced planes such that each of the spaced planes contains four formations 121 formed within the four rail sections 170, with each formation 21 being spaced 90 apart from one another. In the illustrated embodiment, the formations 21 are in the form of notches formed in the rail sections 170.

In other words, to produce a distinct sound signal and pointed impulse, the barrel 112 is provided with multiple flanges or tabs 150, which are spaced angularly around the periphery of the opening 138. Thus, having multiple tabs 150 instead of a single endless formation allows a relatively smaller segment (tab 150) to be substantially more flexible than what would be possible with an endless formation and consequently produces a clear sound signal and pointed impulse upon engagement with the plunger formation 121. As previously mentioned, each tab 150 can have an arcuate shape, as shown in FIG. 16, or the tab 150 can have another shape, such as a polygonal or have any other irregular shape subject only to reliable engagement with the complementary plunger formation (notch) 121. Furthermore, the tabs 150 may be non-uniformly shaped and spaced angularly from one another at a non-uniform distance.

While in the illustrated embodiment, the plunger formations 121 are shown as a plurality of spaced angularly apart indentations or notches, it will be understood that the quality of sound or pointed impulses would not be affected if the plunger formation 121 were formed as an endless indentation (notch), which in this case, there would be a single elongated body as opposed to the plurality of rail section 170.

The rail sections 70 in which the plunger formations 121 are formed are made from flexible material, thereby producing sound signals and pointed impulses to the user's finger due the change of resistance caused by engagement between each plunger formation 121 and each tab or flange 150 associated with the barrel. However, it is equally possible for the tabs 150 to be made from a more rigid material. Regardless of the specific configuration of the tabs 150 and the plunger notches or indentations 121, the width of the indentation 121, as viewed along the longitudinal axis of the device 100, is somewhat greater than a thickness of the tab 150 which improves the quality of sound signals and pointed impulses.

As a result of the plunger 120 having an X-shaped cross-section, each of the axial (longitudinal) rail sections 170 of the plunger 120 extends radially outwards from a center section towards a peripheral edge that defines the central opening 138, as well as towards the flanges or tabs 150. An outer edge 171 of the longitudinal rail sections 170 and the tabs 150 are dimensioned and oriented to radially overlap, which allows the inner wall 158 of the tabs 150 to selectively penetrate the indentations 121 once the tabs 150 and indentations 121 are radially aligned. Each plunger formation can thus be described as being formed of four indentations 121 (that are within the same plane). It will be appreciated that the distance between the indentations 121 along the longitudinal axis of each rail section 170 represents a single dose such that when the complementary and corresponding tab 150 engages one indentation 121 and the user further axially directs the plunger 120 within the central opening 138, the flexible nature of the tab 150 and the force applied to the plunger 120 causes the tab 150 to disengage the indentation 121 and remain in a flexed (stressed) state until the next indentation 121 along the axis of the rail section 70 is axially aligned with tab 150 at which time, the tab 150 engages this next indentation 121. This action of the tab 150 disengaging one indentation 121 and then engaging a next indentation 121 causes one dose to be dispensed as well as the above described sound signal and pointed impulse.

If two or more doses of fluid of predetermined quantity are required, the user continues to move the plunger 120 to generate the desired number of consecutive sound signals and pointed impulses caused by the tabs 150 engaging successive indentations 121 along the axial longitudinal length of the plunger 120. It will be understood that when not engaged within indentations 121, the tabs 150 urge against the outer edges 171 of the rail sections 170, which define the outer surface of the plunger 120. The cross-section of the plunger 120 is not limited to the one shown in FIG. 15, but can have any of circular, polygonal or irregular shapes.

The distal end 122 of the plunger 120 has a seal (not shown) typically made from polymer, such as rubber or plastic, and extending between the outer surface of the plunger 120 and an inner surface of the barrel 112. Penetration of fluid through the seal causes the device 100 to malfunction. Therefore, the seal, displaceable with the plunger 120, presses against the inner surface of the barrel 112 with a force sufficient to prevent fluid from penetration into a space between the seal and the proximal end 116 of the barrel 112.

The components of the dosage device 100 are typically made from engineering plastics. However, various materials may be successfully utilized as well. For example, the barrel 112 and plunger 120 can be made from glass. Alternatively, material of one of these components may be glass, whereas the other component is made from plastic. Furthermore, material of the plunger and barrel may be different from material of the plunger and barrel formations. For example, while material used to form the plunger 120 can include glass, the rail sections 170 in which the formations (indentations 121) are formed can be formed of plastic, and conversely. To implement such a modification technologically, the body of the barrel 112 may be recessed at axially spaced-apart locations, and plastic segments may be removably or fixedly mounted to these recessed locations.

Note that the cross-section of the plunger 120 is not limited to the cross-like shape and can be circular, elliptical, polygonal or irregular. To prevent relative rotation between the plunger 120 and barrel 112, tabs 150 can be dimensioned and shaped to engage the indentations 121. Other configurations of the plunger 120 can be provided with a radial extension, such as a rib, to function similarly to the tab 150.

According to one embodiment, the device 100 of the present invention and in particular, the barrel 112 and the flange member 130 can be formed using a molding process such that the components are integrally formed with one another. More specifically, the barrel 112 and the flange member 130 formed at the proximal end thereof can be conveniently and easily formed by an injection molding process. An injection molding process permits a preselected die to be used with the mold tooling such that the flange member 130 is formed and in particular, the die can has a solid shape with edges that complement and permit the formation of side edges 160 of the upper wall 154. Thus, by providing a different shaped die, the angle D between the two side edges 160 can be varied depending upon the particular application. In addition, the die is shaped so as to form the space 137 between the upper wall 154 and the upper surface 134 of the flange body 132.

By having the upper wall 154 be located at the proximal-most location of the barrel 112, as well as the flange member 130, and by having upper wall 154 define and function as the means for selectively contacting and engaging the plunger formation 121, an injection molding process can advantageously be used to form this interactive part of the device 100 that allows for a predetermined dose to be carefully dispensed as well as provides a sound and axial resistance to alert the user that one dose has been discharged from the device 100. One of the advantages of the design of the present flange member 130 as opposed to other earlier flange designs is that the flexible member (tab 150) that engages and selectively captures and retains the plunger formation 121 is formed at one end of the flange member 130 and therefore, is more conductive to be easily formed by an injection mold die such that it has a specific desired shape.

It will be understood that other techniques can equally be used to form the barrel 112 and the flange member 130 of the present invention and an injection molding technique is merely exemplary of one technique that can be used.

Referring to FIGS. 17-20, a dosage device 200 is configured in accordance with a further embodiment of the invention. Similarly to the device 100 illustrated in FIGS. 13-16, the dosage device 200 has a barrel 210, receiving a plunger 220, and includes complementary barrel and plunger engagement features or formations 230 and 240, respectively. Displacement of the plunger 220 at a distance between axially adjacent plunger formations 240 corresponds to the predetermined fluid dosage entering or exiting the dosage device 200 as described in more detail below.

Displacement of fluid into or from the barrel 210 is associated with sound signals produced by the engaged features/formations 230 and 240 and increased resistance to displacement of the plunger resulting in pointed impulses 220 as a result of engagement between these features 230, 240. The barrel engagement feature 230 is in the form of at least one projection, which is formed on upper surface 134 of the flange 130 and extends radially inward toward the central opening 138. In the illustrated embodiment, there is a pair of projections 230 that are axially aligned with one another and are orientated about 180 degrees from one another.

By having multiple segments (projections 230) instead of a single endless formation (projection) allows a relatively small segment to be substantially more flexible than the endless formation and produce a clear sound signal and pointed impulse upon engagement with the flexible plunger formations (rings) 240. Each segment (projection) can generally have a rectangular shape, as illustrated, or it can have a curved, polygonal or have any other irregular shape subject only to reliable engagement with the flexible plunger rings 240. Furthermore, the segments may be non-uniformly shaped and spaced angularly from one another at a non-uniform distance.

The projection 230 is constructed to selectively mate and engage the plunger formation 240 for releasably locking the plunger 220 in a select location; however, the plunger 220 is easily disengaged from the projection 230 and then can be further axially moved until the projection 230 encounters and engagingly locks with the next plunger formation 240 located axially along the plunger 220. This action results in one dose being dispensed by the device since the dose is defined by the volume between the two plunger formations 240.

According to one embodiment, the projection 230 has a tapered construction such that it is defined by a ramp 232 that is inclined in a radially inward direction from an outer region of the flange 130 toward an inner region thereof. The projection 230 has at one end (a radially inward end) a catch or flange/tab 250 that has an undercut shoulder 252 that serves to engage and retain the plunger formation 240. More particularly, there is a space 254 formed between the shoulder 252 and the upper surface 134 of the flange 130, with the projection formation 140 being disposed and captured within the space 154.

Figure 19:
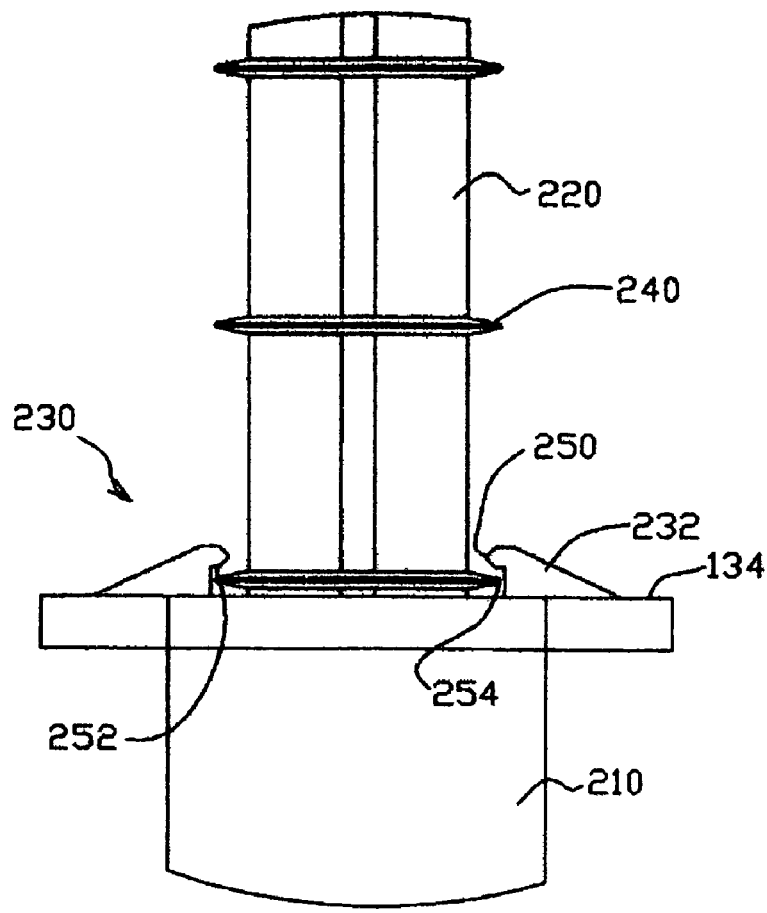
FIG. 19 is an enlarged sectional view taken alone the circle VII of FIG. 18.

By providing at least one pair of projections 230 and locating them opposite one another, the plunger 220 can be securely held at a selected position without experiencing any slippage or undesired movement along the axial direction of the device. As shown in FIG. 19, the plunger formation 240 and the complementary catch 250 can have a beveled construction so as to assist both the engagement and disengagement of the plunger formation 240 relative to the catch 250 when the plunger 220 is moved in an axial direction. More specifically, as the plunger 220 moves in either axial direction, the beveled edge of the plunger formation 240 engages the beveled edge of the catch 250 and this arrangement assists in the disengagement of the captured plunger formation 240 to permit further axial movement of the plunger 220 until the next plunger formation 240 engages the catch 250. At this point, the beveled edges assist in the next plunger formation 240 engaging and sliding into the space 254 where it becomes captured by the catch 250.

As in the previous embodiment, displacement of the plunger 120 relative to the barrel 112 is accompanied by a sound signal and pointed impulse when the barrel and plunger formations engage one another.

In this embodiment, both the projection 230 and plunger formation 240 project from respective inner and outer surfaces of the flange opening 138 and plunger 120, respectively. Also, each of the projections 230 and plunger formations 240 can be segmented in which case, the plunger formation 240 will not be in the form of an annular projection but instead will be in the form of two or more arcuate projections that are orientated so that they engage the projections 130 that are complementary thereto and aligned therewith.

Increased resistance to displacement of the plunger 120 resulting in pointed impulses and generation of sound signals are caused by each catch 250 selectively engaging the plunger formation 240.

Figure 20:
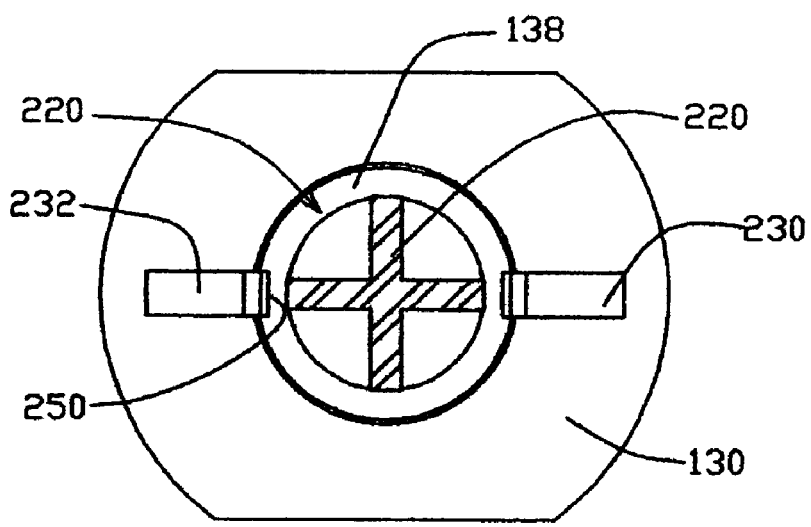
FIG. 20 is a cross-sectional view of the dosage device taken along line VIII-VIII of FIG. 17.

It will be appreciated that the catch 250 overlaps and extends slightly into the central opening 138 of the flange member 130 so as to permit contact between the edge of the plunger formation 240 (annular projection) as the plunger 120 is axially advanced within the central opening 138. The partially overlapping nature of the catch 250 and the plunger formation 240 is shown in FIG. 20.

When the above complementary parts are made from flexible materials, the parts flex during engagement and disengagement, thereby generating a sound signal and a pointed impulse upon engaging one another.

The peripheral edge that defines the central opening 138 of the flange member 130 can be shaped to include a circular portion and two portions (flats) defining a recess which is dimensioned to receive a free end of the plunger's leg (rail structure) 170. As a result, the plunger 120 and barrel 112 are rotationally fixed to prevent the plunger seal from damage. In other words, the flange member 130 and the plunger body can have a keyed type construction so that the plunger body can only be inserted into and axially extend within the flange member 130 and into the interior space 113 when the plunger body (i.e., rail structure) is in registration with complementary locating features formed in the flange member 130.

Figure 21:
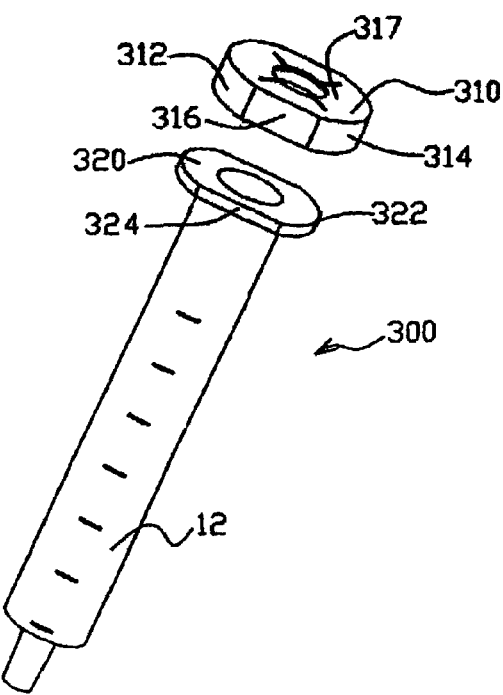
FIG. 21 is an exploded perspective view of a dosage device according to a sixth embodiment with a dosing structure being shown exploded from a syringe barrel.
Figure 22:
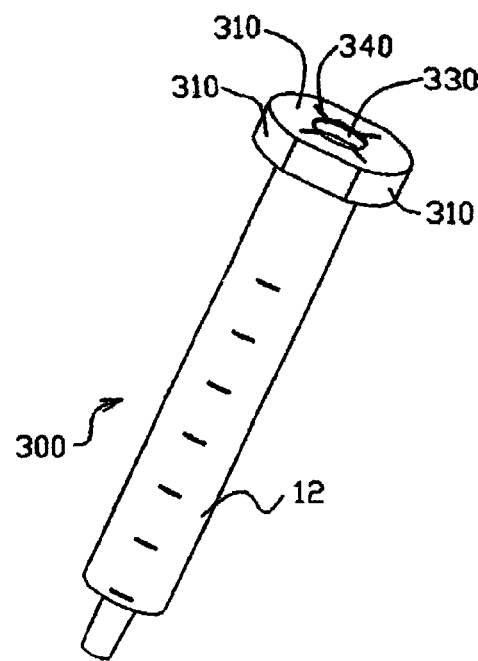
FIG. 22 is a perspective view of the dosage device of FIG. 21 with the dosing structure being attached to the syringe barrel.
Figure 23:
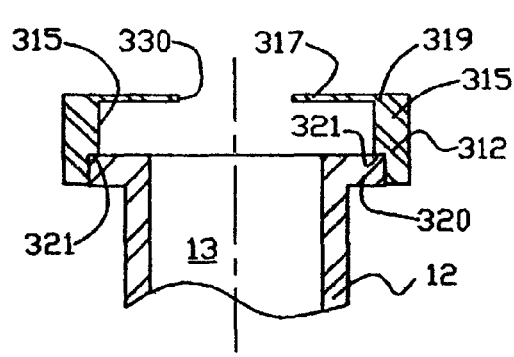
FIG. 23 is a cross-sectional view of the dosing structure attached to the dosage device.

Now referring to FIGS. 21-23 in which a dosage device 300 according to another embodiment is shown. The dosage device 300 has some similarity to the other devices, including device 100, described herein; however, the dosage device 300 is formed to include a dosing cap or member 310 that is a separate member that is easily attachable and removable from the syringe barrel 112. It will be appreciated that the attachability and removeability of the dosing member 310 permits any number of existing conventional syringes to be retrofitted into one of the dosage devices of the present invention by simply securely attaching the dosing member 310 to the barrel 112 of the syringe. The manner of securely attaching the dosing member 310 to the body of the syringe (e.g., an integral flange 320 of the syringe barrel 112) can be accomplished in any number of different ways so long as the dosing member 310 is securely attached to the flange 320. For example and according to one embodiment, the dosing member 310 is attached to the integral flange 320 using a mechanical type fit, such as a snap-fit type arrangement. In this way, the dosing member 310 can easily be snapped onto engagement with the barrel flange 320 and then can be removed by breaking the snap fit attachment.

The cross-sectional view of FIG. 23 illustrates one exemplary snap fit type arrangement where the flange 320 includes a pair of arcuate ends 322 with a pair of parallel sides (flats) 324 being formed therebetween. The flange 320 extends radially outward from the barrel body and this forms a right angle shoulder or lip with the barrel as shown best in FIG. 23. The dosing member 310 is formed of a generally hollow body 312 that has a complementary and similar shape to the flange 320 in that the body 312 of the dosing member 310 includes a pair of arcuate ends 314 and a pair of parallel side portions (flats) 316 formed therebetween.

The hollow body 312 is formed of an upstanding (vertical) peripheral wall 315 and an upper wall or ceiling 317 that is formed at an upper edge 319 of the upstanding peripheral wall 315 and extends thereacross. As best shown in FIG. 23, the peripheral wall 315 has a shoulder or undercut 321 formed in the peripheral wall 315 along a lower edge 323. More specifically, the shoulder 321 is formed at least in the peripheral wall 315 at the arcuate ends 314 thereof to permit the dosing member 310 to be securely attached to the barrel flange 320 as by a mechanical fit (snap fit). The shoulder 321 can also be formed in the two side portions 316 of the body 312 and in this case, the snap fit attachment between the dosing member 310 and the flange 320 is formed generally around an entire periphery of the dosing member 310.

As shown in FIGS. 21-23, the dosing member 310 has an opening 330 formed therethrough. The opening 330 is formed in a central area thereof through the upper wall 317 and into an interior space defined by the peripheral wall 315. The opening 330 is axially aligned with the interior 113 of the barrel 112 to permit the plunger 120 to enter and be axially displaced within the barrel 112. The opening 230 can take any number of different shapes, with the illustrated shape being a circle or an oval; however, other shapes are possible so long as the shape is complementary to the plunger. The upper wall 317 includes a plurality of cuts or slits 340 formed therein around the periphery of the opening 330. More specifically, the slits 340 extend radially outward from the opening 330, with one end of each slit 340 being in communication with the opening 330. The other end of the slit 340 is spaced from the upper edge where the upper wall 317 joins the upstanding peripheral wall 315. In the illustrated embodiment, there are four slits 240 formed around the opening 330, with each slit 340 being formed generally in four corner sections of the dosing member 310. In other words, the slits 340 can be formed so that they are diagonally opposite one another (i.e., two pairs of slits with one slit in one group being 180 degrees opposite the other slit of the pair).

As best shown in FIG. 23, the opening 330 occupies an area that is less than the area occupied by the interior space 113 of the barrel 112. In other words, the dimensions (e.g., diameter) of the opening 330 are less than the dimensions (e.g., diameter) of the interior space 113. Thus, when the dosing member 310 is attached to the flange 320, the peripheral edges of the upper wall 317 that define the opening 330 slightly protrude into the interior space 113 defined in the barrel 112 so that as the plunger 120 axially moves within the interior space 113, the plunger 120 and more particularly, the plunger formations 121 thereof contact and engage the upper wall 317 as described below.

These slits 340 create weak points in the upper wall 317 as well as partitioning the upper wall 317 into a number of discrete segments. By introducing weak points into the upper wall 317 and segmenting the upper wall 317, the discrete segments are permitted to have some flexing action which in turn permits the selective engagement and capturing of one plunger formation 121 (FIG. 13) as the plunger 120 is axially advanced within the barrel 112. Accordingly and similar to the previous embodiments, the flexing of the segments permits the plunger projection (ring) 121 to be captured underneath the segments resulting in the plunger 20 being held in one position. To dispense a dose of predetermined quantity, the user simply axially advances the plunger 120 toward the distal end 114 of the barrel 112, thereby causing the projection 121 to disengage from the segments due to the flexing action thereof and then axially advance until the next plunger projection 121 engages and is captured underneath the segments (resulting in an audible noise and a pointed impulse being generated). As with the previous embodiments, the movement of the plunger 120 in an axial direction causing the segment to disengage from one projection 121 and engage the next projection 121 results in a single dose being dispensed; however, if it is desired to dispense more than one dose, the user simply advances the plunger 120 so that the segments of the upper wall 317 successively engage multiple plunger projections 121, thereby dispensing multiple doses.

Figure 24:
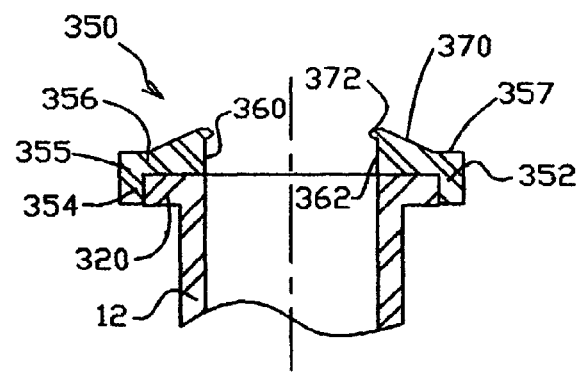
FIG. 24 is a cross-sectional view of a dosing structure according to a seventh embodiment attached to the dosage device.

FIG. 24 shows another embodiment of a removable dosing member or cap 350 that is similar to the dosing member 310. The illustrated dosing member 350 does not include a shoulder or undercut formed in its lower body to assist in coupling the dosing member 350 to the flange 320 as included in the dosing member 310. Instead, the dosing member 350 has a body 352 that includes an upstanding (peripheral or vertical) wall 354 and an upper wall or ceiling 356 that extends inwardly from an upper edge 355 of the upstanding wall 354. In this embodiment, an inner surface of the peripheral wall 354 is flat and does not include an undercut or shoulder formed therein but instead is coupled to the flange 320 by a mechanical fit. More particularly, an interference or frictional fit is formed between the dosing member 350 and the flange 320. Once the dosing member 350 is securely attached to the flange 320 it is removed by the user applying a force that overcomes the frictional force between the two parts.

The upper wall 356 extends radially inward and includes an opening 360 formed therein, preferably in a central location thereof. The opening 360 can have any number of different shapes, such as a circle or oval, etc., so long as the shape is complementary to the size and shape of the plunger 120. The opening 360 is defined by an edge 362 that defines the inner boundary of the upper wall 356. As illustrated in FIG. 24, the inner edge 362 is axially aligned with (flush with) the inner surface of the barrel 112.

Unlike the embodiment of FIGS. 21-23, an upper surface 357 of the upper wall 356 is not a flat, planar surface but rather includes an incline or ramp 370 that is upwardly (positive) inclined toward the opening 360. At the top of the ramp 370, a flange, protrusion or catch 372 is formed and protrudes inwardly into the opening 360. If the protrusion 372 extends completely around the opening 360, the protrusion 372 is in the form of an annular flange or tab that extends around the inner surface of the upper wall 356. As with the previous embodiments, the protrusion 372 acts as an interference member that selectively engages the plunger 120 and more particularly, one of the plunger formations 121, as a means for controllably dispensing one or more doses from the device. It will be understood that the protrusion 372 can be segmented as opposed to being an endless protrusion that extends around the opening 360.

In operation, the plunger is displaced towards and presses against the proximal end of the barrel to assume an initial position. Displacement of the plunger towards the distal end of the barrel 112 is accompanied by a number of sound signals and pointed impulses as each of the plunger formations 121 passes the formation 121 formed on the barrel's flange 320. As disclosed, each sound and/or change of resistance is indicative of a predetermined dosage of fluid filling the barrel 112. Reverse displacement of the plunger 120 towards the proximal end of the barrel 112 is also accompanied by indicating signals informing the user how much liquid has been administered.

While the dosage device of the invention has been described to be adapted for injection, it may be applicable to other systems, angiographic and otherwise. Furthermore, application of the inventive dosage device can be successfully utilized in various industries requiring a metered distribution of fluid or other matter. Thus the foregoing description and accompanying drawings set forth the preferred embodiment of the invention. Modifications, alternative designs will be apparent in light of the foregoing teaching without departing from the scope of the appended claims.

What is claimed is:

1. A dosage device comprising:
a barrel extending along a longitudinal axis and including an interior space; a flange member extending outwardly from the barrel, the flange member including at least one flexible tab, wherein a space is formed below the flexible tab, the space being laterally open to an exterior of the barrel and freely accessible along an exterior surface of the flange; and
a plunger received in and axially displaceable within the interior space; and at least one plunger formation provided on an outer surface of the plunger, wherein the at least one plunger formation is configured to selectively engage the flexible tab while generating an indicating signal corresponding to a predetermined dosage of fluid drawn into or dispensed from the barrel during axial displacement of the plunger.

2. The dosage device of claim 1, wherein there are two plunger formations and two flexible tabs located opposite one another, the flexible tabs defining in part a pair of openings that form entrances into the space.

3. The dosage device of claim 2, wherein the openings are defined in part by a pair of vertical walls, the flexible tabs being formed at upper ends of the vertical walls spaced from a floor of the flange.

4. The dosage device of claim 3, wherein the flexible tabs are disposed parallel to the floor.

5. The dosage device of claim 1, wherein a portion of the plunger below the flexible tab is visible through the space.

6. The dosage device of claim 3, wherein the flexible tabs, vertical walls and the floor are part of an integral structure.

7. A dosage device comprising:
a barrel extending along a longitudinal axis and including an interior space and a flange member, the flange member including at least one inwardly extending flexible tab that is spaced above a floor of the flange, the floor including an opening that forms an entrance into the interior space, wherein a space is formed between the flexible tab and the floor, the space being open to the exterior of the barrel along a side of the flange so that the space is externally accessible along the side of the flange member; and
a plunger received in and axially displaceable within the interior space; and at least one plunger formation provided on an outer surface of the plunger, wherein the at least one plunger formation is configured to selectively engage the flexible tab while generating an indicating signal corresponding to a predetermined dosage of fluid drawn into or dispensed from the barrel during axial displacement of the plunger;
wherein a portion of the plunger below the plunger formation is externally visible through the space.

8. The dosage device of claim 7, wherein there are two plunger formations and two flexible tabs located opposite one another, the flexible tabs defining a pair of openings that form entrances into the space.

9. The dosage device of claim 7, wherein the openings are defined in part by a pair of vertical walls, the flexible tabs being formed at upper ends of the vertical walls spaced from the floor of the flange that is defined at lower ends of the vertical walls.

10. The dosage device of claim 7, wherein the flexible tabs are disposed parallel to the floor.

11. The dosage device of claim 7, wherein the flange is integrally formed at a proximal end of the barrel.

* * * * *